(12) United States Patent
Lau et al.

(10) Patent No.: US 8,121,672 B2
(45) Date of Patent: **\*Feb. 21, 2012**

(54) ELECTROSTATIC DISCHARGE PROTECTION FOR WRIST-WORN DEVICE

(75) Inventors: Bill Lau, Daly City, CA (US); Thomas Ying-Ching Lo, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 908 days.

This patent is subject to a terminal disclaimer.

(21) Appl. No.: 12/139,190

(22) Filed: Jun. 13, 2008

(65) Prior Publication Data

US 2009/0312656 A1    Dec. 17, 2009

(51) Int. Cl.
*A61B 5/04* (2006.01)
(52) U.S. Cl. ........................................... 600/509
(58) Field of Classification Search .................. 600/509, 600/483, 485, 520; 340/573.1
See application file for complete search history.

(56) References Cited

U.S. PATENT DOCUMENTS

| | | | |
|---|---|---|---|
| 4,747,086 A | 5/1988 | Shaw | |
| 5,365,935 A * | 11/1994 | Righter et al. | 600/523 |
| 5,691,962 A | 11/1997 | Schwartz et al. | |
| 2002/0012291 A1 | 1/2002 | Robinett | |
| 2005/0243653 A1 | 11/2005 | Lizzi | |
| 2011/0181422 A1 * | 7/2011 | Tran | 340/573.1 |

\* cited by examiner

*Primary Examiner* — George Manuel
*Assistant Examiner* — Robert Wieland
(74) *Attorney, Agent, or Firm* — Vierra Magen Marcus & DeNiro LLP (57) ABSTRACT

Electro static discharge (ESD) protection is provided for electronic devices with integrated circuits, such as for example heart rate monitors. The ESD protection protects against voltage accumulation and discharge through device external parts that are connected to internal device circuitry. The ESD protection isolates the internal device circuitry and provides a low impedance path over which electro static charges and any transient voltages in the device may discharge. The integrated circuits, electrical components, and other parts protected from ESD may be connected to monitor circuitry and be externally exposed, such as sensing or measurement parts exposed outside the device. The external parts may include a sensing case back, sensing push-buttons, or other components that provide a signal to or are otherwise in communication with the internal device circuitry.

20 Claims, 7 Drawing Sheets

ELECTROSTATIC DISCHARGE PROTECTION FOR WRIST-WORN DEVICE

BACKGROUND

Circuit fabrication technology has allowed integrated circuits to have extremely small sizes. These small integrated circuits are susceptible to voltages applied to the circuits as electro static discharges. When electro static charges accumulate in a device component, they create a high voltage that may discharge into the integrated circuit or electrical system. By discharging into the circuit, the applied voltage can alter the state of the circuit or cause damage to the circuit.

Electro static charges may create a high voltage to ionize the air in its vicinity and thus create a low impedance path to discharge the energy. The transient current that is created in a very short instant of time can damage electronic components.

SUMMARY

Electro static discharge (ESD) protection is provided for electronic devices with integrated circuits, such as for example heart rate monitors. The ESD protection protects against voltage accumulation and discharge through device external parts that are connected to internal device circuitry. The ESD protection bypasses the internal device circuitry and provides a low impedance path over which electro static charges and any transient voltages in the device may discharge. In some embodiments, to the ESD protection circuitry may provide a high impedance path to block or to attenuate the transient discharge current that may go through the internal device circuitry. This may also effectively protect the device circuitry from high voltage transient damage.

The integrated circuits, electrical components, and other parts protected from ESD may be connected to monitor circuitry and be externally exposed, such as sensing or measurement parts exposed outside the device. For example, the external parts may include a sensing case back, sensing push-buttons, or other components that provide signals to or are otherwise in communication with the internal device circuitry.

Voltage suppression or voltage discharge circuitry may be used to implement the ESD protection. The voltage suppression circuitry may be any circuitry, component or device that bypasses the internal heart rate monitor circuitry and provides a low impedance path to ground or some other safe node within the device. In some embodiments, the voltage suppression circuitry may be a diode or some other device. In other embodiments, the voltage suppression circuitry may be a resistor to block or to attenuate voltage transient from the internal device circuitry This summary is provided to introduce a selection of concepts in a simplified form that are further described below in the description. This summary is not intended to identify key features or essential features of the claimed subject matter, nor is it intended to be used as an aid in determining the scope of the claimed subject matter.

DETAILED DESCRIPTION

The technology herein provides for electro static discharge (ESD) protection for heart rate monitors and other electronic devices with integrated circuits. The protection mechanism protects against voltage accumulation and discharge through device external parts which are connected to internal device circuitry. The ESD protection bypasses the internal device circuitry and provides a low impedance path over which electro static charges and any transient voltages in the device may discharge. In some embodiments, the ESD protection circuitry may provide a high impedance path which blocks or attenuates the transient discharge current that may go through the internal device circuitry. This may also effectively protect the device circuitry from high voltage transient damage.

The integrated circuits, electrical components, and other parts protected from voltage discharge may be connected to monitor circuitry and be externally exposed. In some embodiments, the exposed parts may be signal sensing or measurement components. For example, the external parts may include a sensing case back, sensing push-buttons, or other components that provide signals to or are otherwise in communication with the internal device circuitry.

Voltage suppression or voltage discharge circuitry may be used to implement the ESD protection within a heart rate monitor or other device. The voltage suppression circuitry may be any circuitry, component or device that bypasses the internal heart rate monitor circuitry and provides a low impedance path to ground or some other safe node within the device. In some embodiments, the voltage suppression circuitry may be a diode or some other device. In some embodiments, the voltage suppression circuitry may include a resistor to block or to attenuate voltage transient from the internal device circuitry The voltage suppression circuitry, or voltage discharge circuitry, may be implemented in a heart rate monitor configured in one of several ways. For example, typical sports watches do not have externally exposed metal portions except the case back, which is typically not used as a sensor that connects to the internal circuitry, and a clamp is used to maintain the position of a battery with respect to the circuitry of the watch. To manufacture the watch, the manufacturer will usually use a clamp that holds the module from bottom up. In this configuration, the positive end of the battery will be facing down (towards the case back and away from a display on the top of the watch) so that when the watch back is opened, it is easier to replace the battery. When a battery positive terminal is electrically and mechanically connected to the clamp, the microcontroller has to be wired for a pull-down configuration. The simplest way to provide ESD protection in typical sports watches is to connect the clamp to the case back directly. There is no need to provide any discharge circuitry, and to do so would not be economical. For the EKG heart rate monitor of the present technology, both bottom-up or top-down clamps are all possible, as well as pull-up or pull-down heart rate monitor circuit configurations. Thus, in some embodiments, for each combination used in a heart rate monitor, the discharge circuitry may include high impedance component, such as a resistor, to effectively protect the module as well as an ESD protection diode for every sensor.

Figure 1:
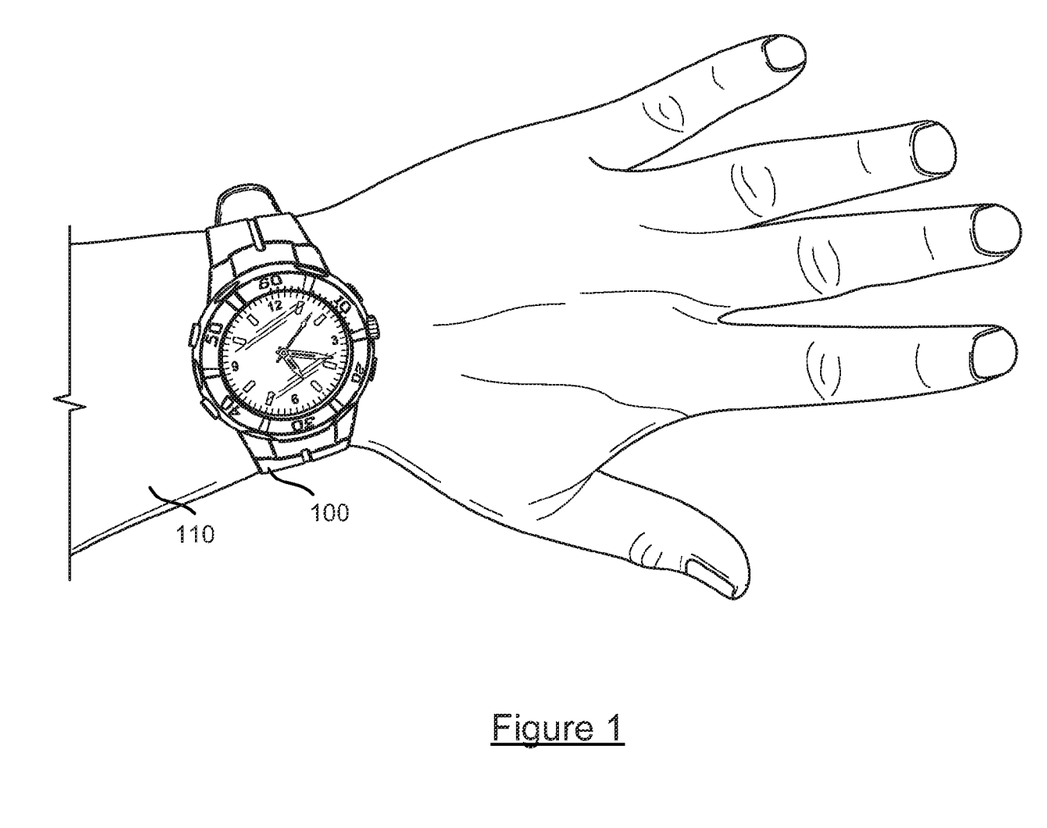
FIG. 1 is an illustration of a wrist worn heart rate monitor worn by a user.

FIG. 1 is an illustration of a wrist worn heart rate monitor 100 worn on the wrist of a user 110. The monitor 100 may include a case back (not shown) positioned on the back of the monitor and in contact with the user. Moreover, the heart rate monitor 100 may include several push buttons which extend outside the casing of the monitor.

Figure 2A:
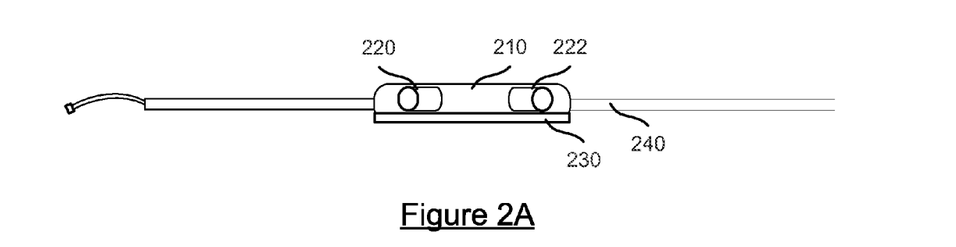
FIG. 2A is an illustration of a side view of a wrist worn heart rate monitor.

FIG. 2A is an illustration of a side view of a wrist worn heart rate monitor. The heart rate monitor of FIG. 2A includes watch case 210, push-buttons 220 and 222, watch case back 230 and a heart rate monitor band 240. Watch case 210 contains the internal components of the heart rate monitor, such as for example circuitry, one or more plastic housing pieces and a metal clamp which may keep the internal components together, such as for example heart rate monitor circuitry, a display and other system components such as the battery. In some embodiments, two plastic housing pieces are used within the monitor. Push-buttons 220-222 allow the user to provide input to circuitry of the watch. In particular, the user may depress one or more buttons inward towards the watch case. The push-buttons may be implemented as sensing devices which detect a user's heart rate, body fat or some other user biometric. These push buttons can also be implemented as mode activating mechanisms to set time, manage a chronograph and alarms, and other watch and heart rate monitor functions. Push buttons can also be implemented to be accessed from the watch top and serve as a sensor device.

Watch case back 230 is attached to the back of the heart rate monitor and may be in contact with a surface of a user. In some embodiments, watch case back 230 may be a sensing device in addition to encasing the monitor components. For example, the case back may be used to transmit and receive signals to and from a user to determine body temperature, heart rate, body fat or some other user biometric.

Figure 2B:
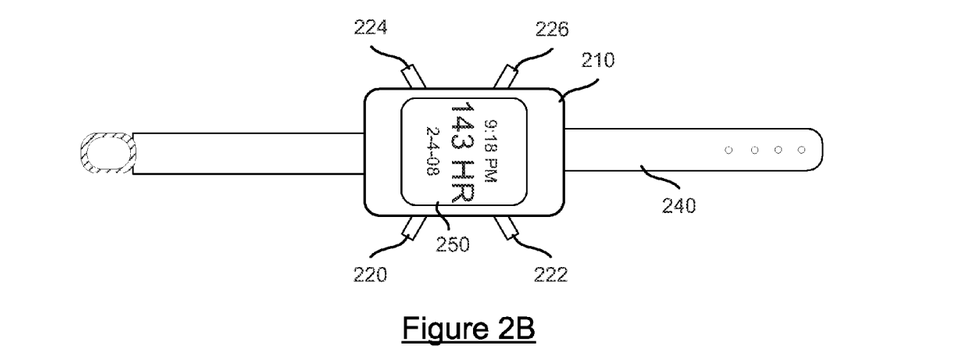
FIG. 2B is an illustration of a top view of a wrist worn heart rate monitor.

FIG. 2B is an illustration of a top view of a wrist worn heart rate monitor. The heart rate monitor of FIG. 2B includes heart rate monitor case 210, push-buttons 220, 222, 224 and 226, heart rate monitor band 240 and display portion 250. Push-buttons 220-222, heart rate monitor case 210 and band 240 of the FIG. 2B are the same as those discussed above with respect to FIG. 2A. Display portion 250 displays information as determined by circuitry within the monitor regarding the current time, date, heart rate of the user, and/or other information. Buttons 224 and 226 may be depressed towards case monitor case 210 to invoke a mode selection input such as switching between date, time, stopwatch, and so on, or invoke some other action or state provided by the monitor device. For instance, a heart rate monitor watch can use push buttons 222 and 224 as sensors. When both are depressed at the same time, a heart rate mode will be activated. During the heart rate mode, an EKG signal maybe simultaneously sensed by 222, 224 and 230 as a regular 3-lead EKG monitor. The sensed EKG signals are then processed and a heart rate reading will be shown on 250.

Figure 3:
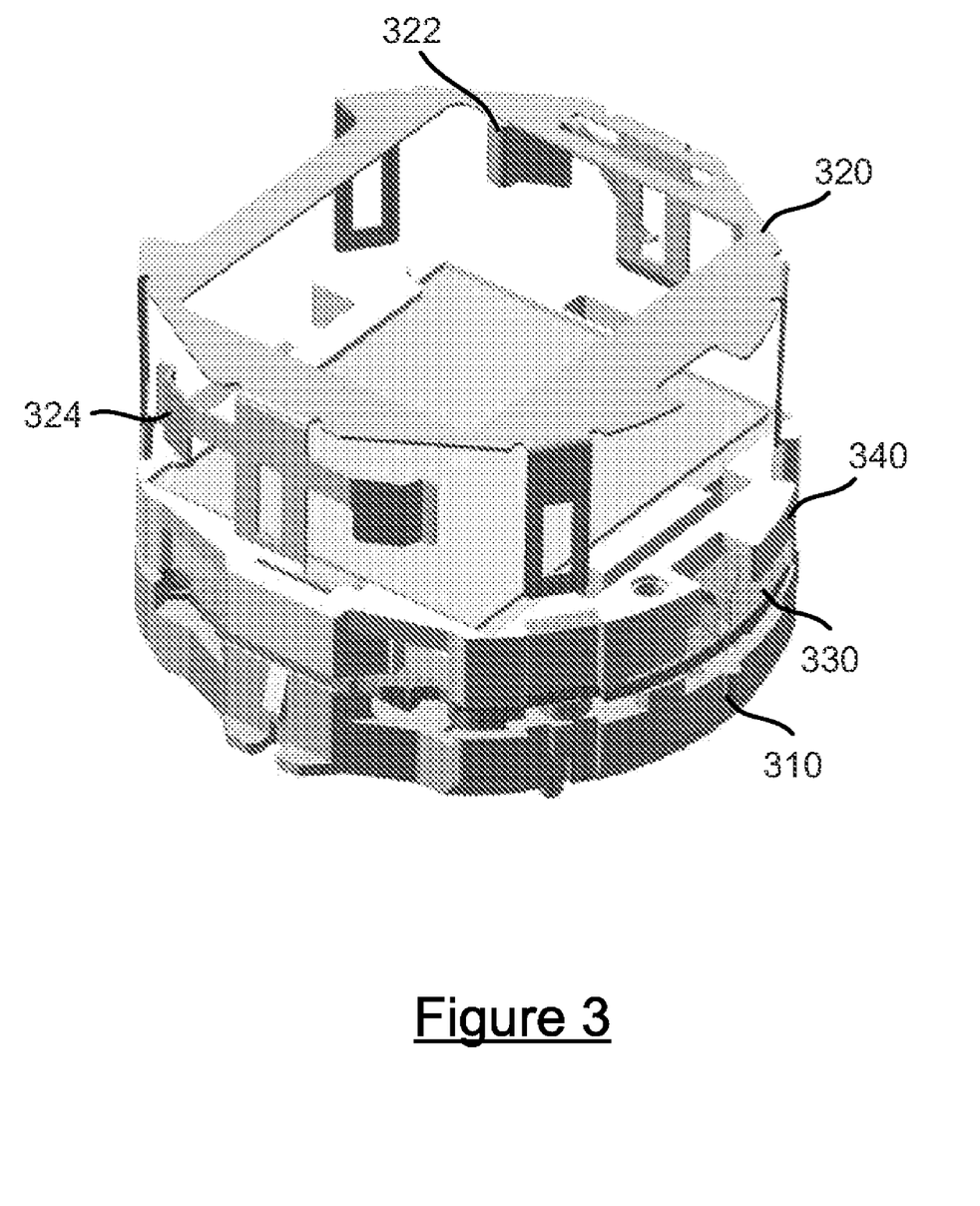
FIG. 3 is an illustration of a watch module clamp attached to watch circuitry.
Figure 4:
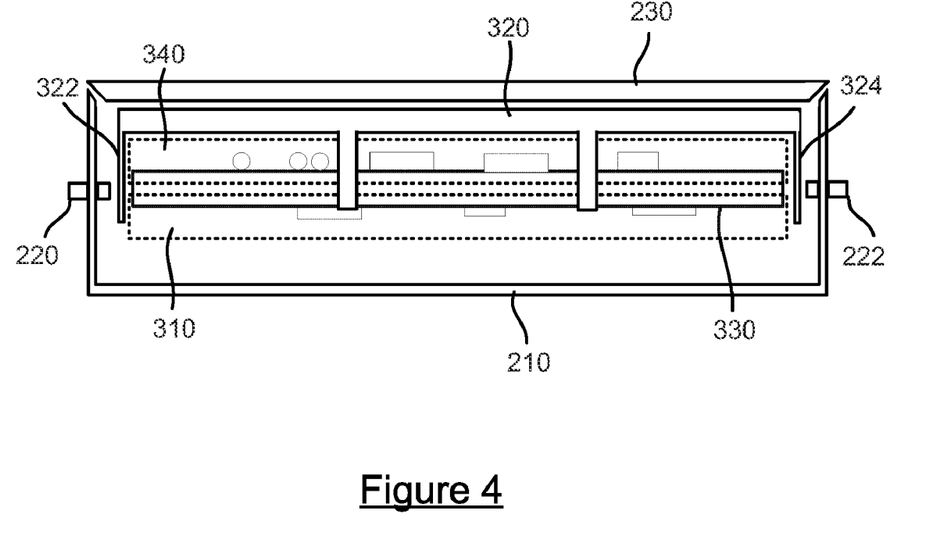
FIG. 4 is an illustration of a cutaway side view of a heart rate monitor.

Within a typical wrist worn watch or a heart rate monitor, a clamp may be used to secure two plastic housings, a printed circuit board, a display unit and a battery to form a watch module. The module is placed into a watch case having one to four side push buttons built-in. Two portions of wrist bands are attached to the watch case to form a finished wrist watch as in FIG. 2B. FIGS. 3 and 4 provide illustrations of possible configurations of wrist worn heart rate monitor modules.

FIG. 3 is an illustration of a watch module clamp attached to watch circuitry and includes module clamp 320, plastic housing 310 and 340 and heart rate monitor circuitry 330. Plastic housing 310 and 340 have molded cavities to accommodate an opto-electric display such as LCD, LED and a battery. For example, the housings can be used to encase and hold in place heart rate monitor circuit 330. The clamp is illustrated as being removed and positioned directly above the monitor circuitry, implementing a top-down configuration. In another embodiment, the clamp can be positioned directly under the monitor circuit (in a bottom up configuration) as depicted in FIG. 4. As illustrated in FIG. 3, module clamp 320 is used to fasten plastic housings 310 and 340 and the heart rate monitor circuit 330 together into a module. The clamp has one or more extensions, such as for example extensions 322 and 324, which are positioned near an edge of the circuit 330. The edge of the circuit between the top and the bottom surfaces of circuit board 330 can be implemented as an electrical contact and plated with gold near extensions 322 and 324. When a push button is pressed, the push button makes contact with an extension which in turn makes contact with the gold plated surface of the circuit edge. Thus, each clamp extension may be viewed as a portion of a switch which closes a circuit when a push button is sufficiently depressed by a user to make contact with the gold plated edge of the circuit, thereby invoking a state change in the circuitry. Operation of heart rat monitor circuitry is discussed with respect to FIGS. 5 and 6 below.

FIG. 4 is an illustration of a cutaway side view of a heart rate monitor. The heart rate monitor of FIG. 4 includes heart rate monitor case 210, push-buttons 220 and 222, heart rate monitor case back 230, module clamp 320, clamp extensions 322 and 324, plastic housing 310 and 340 and heart rate monitoring circuit 330. Plastic housing portions 310 and 340 are illustrated with dotted lines to indicate that they are encompass portions of circuitry 330. As illustrated, case back 230 is positioned against heart rate monitor case 210 and push-buttons 220-222 may be configured to extend through the monitor case. When depressed, push-buttons 220 and 222 initially make contact with clamp module extension 322 and 324, respectively. When a button is sufficiently depressed, the button displaces a clamp module extension until the extension makes contact with a corresponding portion of circuit 330, such as for example a side edge of the circuit that is gold plated. When contact is made between an extension displaced by a push button and the circuit, the contact closes a circuit switch within the circuit. Circuit operation with switches closed by depressing a push button is discussed below with respect to FIGS. 5 and 6.

Figure 5:
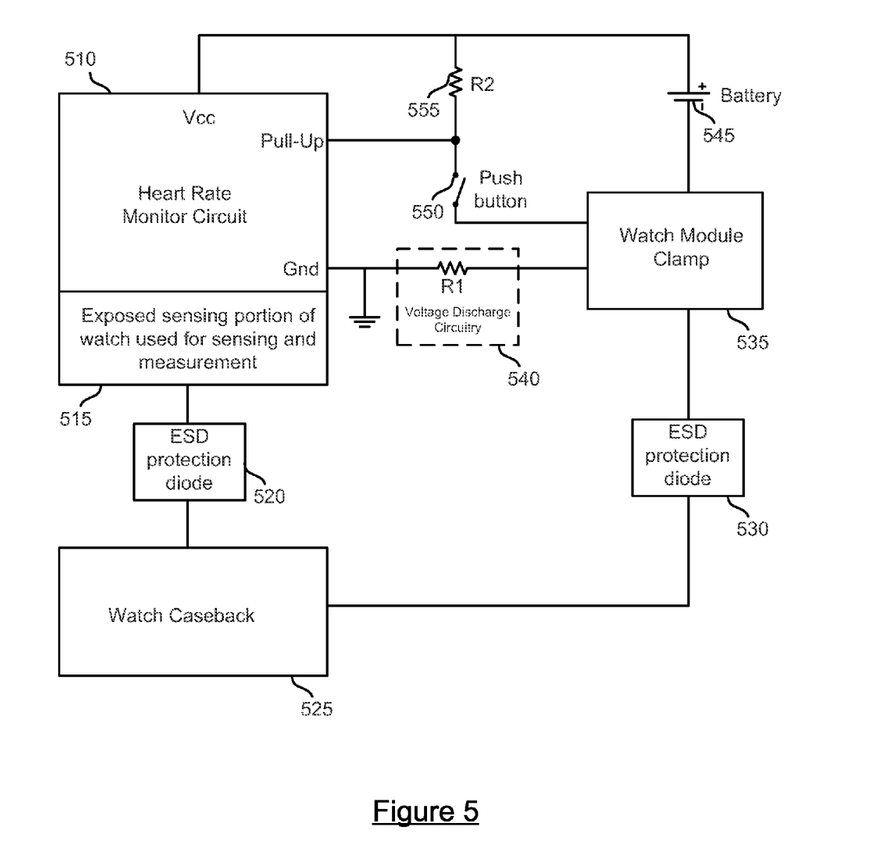
FIG. 5 is a block diagram of an embodiment of a heart rate monitor with voltage discharge circuitry.
Figure 6:
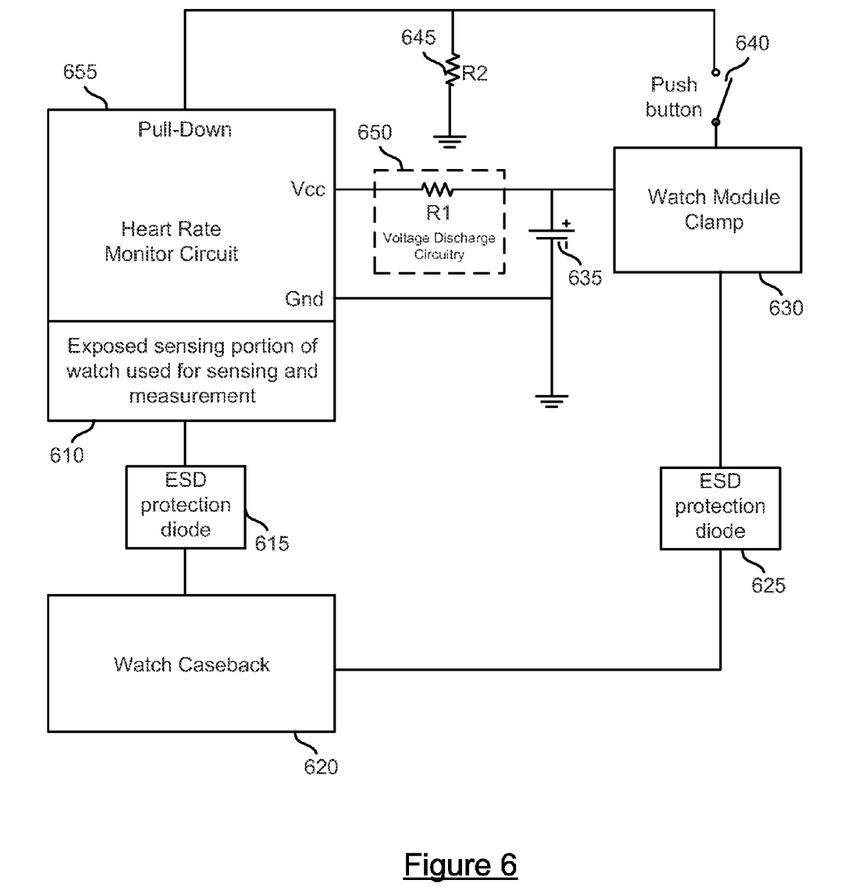
FIG. 6 is a block diagram of another embodiment of a heart rate monitor with voltage discharge circuitry.

For wrist worn devices, such as a wrist worn heart monitor watch device, ESD protection may be achieved by isolating outer portions of the device from circuitry which can be damaged by transient voltage discharges or electro-static discharges. With more advanced wrist worn electronic devices that contain external components such as vital sign sensors connected to internal device circuitry, outer portions of the device are often exposed to electrostatic discharge and thus make the internal circuit they connect to vulnerable to damage from the discharges. These advanced devices require protection not provided in typical wrist worn devices. FIGS. 5 and 6 illustrate block diagrams of embodiments of heart rate monitors that provide electro-static discharge and other transient voltage protection for wrist worn devices having external parts connected to internal device circuitry.

The ESD protection diode can be any fast Zener diode, Schottky diode or Transient Voltage Suppressor diode, or other suitable diodes. A partial list of examples of suitable diodes includes a Comchip TV06B100JB-G Bi-directional single diode, On Semi DF6A6.8FUT1G Uni-directional TVS Array diode and NUP4102XV6 Bi-directional TVS Array diode, Comchip CEBS065V0-G Bi-directional TVS Array diode, Samtech RCLAMP0521P Bi-directional TVS single diode and SMF3.3 Uni-directional TVS Array diode, and Vishay SMF5V0A Uni-directional TVS single diode, VESD05C-FC1 Bi-directional TVS single diode and VESD05A5a-HS3 Uni-directional TVS array diode.

FIG. 5 is a block diagram of an embodiment of a heart rate monitor with voltage discharge protection circuitry. The block diagram of FIG. 5 includes heart rate monitor circuit 510, exposed sensing portions 515, ESD protection diodes 520 and 530, watch case back 525, watch module clamp 535, battery 545, one or more push buttons 550, R2 resistor 555 and voltage discharge circuitry 540.

Heart rate monitor circuit 510 includes inputs of Vcc, pull-up I/O port, and ground. The Vcc input is connected to R2 resistor 555 and the positive terminal of battery 545. The pull-up input of heart rate monitor circuit 510 is connected to the other end of R2 resistor 555 and an end of switch 550. Switch 550 may be implemented as any mechanism that, when engaged, closes a circuit between the ends of the switch. For example, the switch may be implemented as a side mounted or top mounted push button or some other depressible switch or mechanism. This end of the switch represents the actual gold plated edge surface of the circuitry 330 in FIGS. 3 and 4. The other end of the switch that is connected to the watch module clamp represents the extensions 322 and 324. The ground input of heart rate monitor circuit 510 is connected to ground and one end of voltage discharge circuitry 540.

Heart rate monitor circuit 510 may also be connected to one or more exposed sensing portions 515 used for sensing and/or measurement. Each exposed sensing portion may be connected to an ESD protection diode 520, and each protection diode is connected to watch case back 525. The sensing portions may be implemented as metal or some other conductive material, and may be configured to extend from the surface of the monitor or comprise a surface of the monitor. In some embodiments, the cathode of each ESD protection diode is connected to case back 525.

Watch module clamp 535 is connected to the negative terminal of battery 545, the other end of push button switch 550 and the other end of voltage discharge circuitry 540. Additionally, clamp 535 may be connected to watch case back 525 through an ESD protection diode 530. In one embodiment, similar to diode 520, protection diode 530 has the cathode end connected to watch case back 525 and the anode connected to clamp 535 as one embodiment.

Voltage discharge circuitry 540 is connected to the ground connection of heart rate monitor circuit 510 and watch module clamp 535. The circuitry may be any circuitry or component that provides a high impedance path to an electro static charge and/or transient voltage that occurs from the watch module clamp. This usually happens when electro static charge is built up in a person wearing a watch. For example, when one or more of the side push buttons are near a metal object such as a door knob, the discharge may occur through the air gaps between the side pushers and the extensions of the metal clamp. By implementing the high impedance path between the clamp and the heart rate monitor circuit, the discharge or transient voltage occurring at watch module clamp 535 will go through the preferred lower impedance path comprising ESD protection diode 530 to the watch case back and through the human body to earth ground. (Human body and earth ground are not shown in FIG. 5 and FIG. 6) Thus, this voltage discharge circuitry attenuates the ESD transient so that it doesn't damage heart rate monitor circuit 510, which contains both analog amplifier circuitry and digital microcontroller integrated circuit. In some embodiments, voltage discharge circuitry may be implemented as a resistor, diode or some other component.

The block diagram of FIG. 5 is configured as a pull-up configured circuit with a micro-controller integrated circuit and is illustrated with a single switch push button switch 550 corresponding to a push button. The circuit of FIG. 5 is intended as an example only and may be implemented with more switches and corresponding push buttons (for example any of push buttons 220-226).

The operation of the circuit of FIG. 5 is as follows. Under normal conditions when the heart rate mode is not active, battery 545 provides very little power to the heart rate monitor circuit. The positive side of the battery is applied at Vcc input to 510. The current, therefore, goes through heart rate monitor circuit 510 from the Vcc input to the Gnd terminal, through voltage discharge circuit 540, watch module clamp 535 and back to the negative side of the battery 545 to complete the circuit loop. In some embodiments, this closed loop associated with the normal operation of the watch corresponds to the microcomputer in the monitor circuit 510 operating in a time keeping mode as in a standard wrist worn sports watch. The low current with the magnitude of a few microamperes going through the voltage discharge circuit R1, 540, creates a very small and negligible voltage drop across 540.

When a push button switch such as 550 is closed to activate heart rate mode, for example, the microcontroller chip in heart rate monitor circuit 510 will operate in a high speed mode in order to sample and process EKG signals at sensors 515. When operating in this mode, the operating current is higher and the voltage drop across voltage discharge circuitry 540 will be more than in the inactive or idle state. The impedance of voltage discharge circuitry can be selected to avoid excessive voltage drop across 540, for example such that the actual operating voltage between Vcc and Gnd terminals in 510 would be lower than the minimum operating voltage required.

Under normal operating conditions a circuit loop is formed between the positive terminal of battery 545, heart rate monitor circuit 510, watch module clamp 535, voltage discharge circuitry 540 and ground. As a result, there is a voltage drop across voltage discharge circuitry 540. When voltage discharge circuitry 540 is implemented as resistor R1, the voltage drop across R1 resistor 540 from watch module clamp 535 to ground is the total current running through R1 times the value of R1 according to Ohm's Law.

In some embodiments, when a resistor R1 is used to implement voltage discharge circuitry 540, the circuit is designed such that the value of the R1 resistor and current passing through the resistor is small enough to avoid causing a substantial voltage drop to affect heart rate circuit 510 performance. For instance, if it is determined that the maximum operating current of the device under high sampling rate for heart rate monitoring is 1 milliampere and the allowed maximum voltage drop across R1 is 100 millivolts or 0.1 volt without affecting circuit performance, then the value of R1 can be as high as 100 ohms. When the device is not in heart rate mode but in time keeping mode, for instance, the operating current is usually less than 10 microamperes. Therefore, the voltage drop across a 100-ohm resistor will be only 1 millivolt which is negligible.

When an electrostatic discharge or other transient voltage discharge occurs at watch module clamp 535 through the air gap between one of the side pushers and the clamp, the charge will partly dissipate through resistor 540 and mostly through ESD protection diode 530, to watch case back 525, and then going through the human body to earth ground. By placing the resistor between clamp 535 and circuit ground, the circuit is protected from unwanted electro-static discharge and transient voltage discharges.

When an electro static discharge or other transient voltage discharge occurs at exposed sensors 515, the charge will go through the ESD protection diode 520 to watch case back 525 such that heart rate monitor circuit 510 is not affected. This is because protection diode 520 presents a much lower impedance path than the heart rate monitor circuit 510 for the charge to go through.

FIG. 6 is a block diagram of another embodiment of a heart rate monitor with voltage discharge circuitry. The system of FIG. 6 includes heart rate monitor circuit 655, exposed metal portions 610, ESD protection diodes 615 and 625, watch case back 620, watch module clamp 630, R2 resistor 645, battery 635, push button switch 640 and voltage discharge circuitry 650. The system of FIG. 6 includes a heart rate monitor circuit 655 implemented in a pull-down configuration with a watch module clamp connected to the positive terminal of the battery.

Heart rate monitor circuit 655 includes inputs of ground, Vcc and pull-down. The ground input is connected to ground and the negative terminal of battery 635, the Vcc input is connected to one end of voltage discharge circuitry 650, and the pull down input is connected to one end of R2 resistor 645 and one end of the push button switch 640. The other end of resistor R2 is connected to ground and other end of push button switch 640 is connected to watch module clamp 630. Clamp 630 is also connected to the positive terminal of battery 635, the other end of voltage discharge circuitry 650, and the anode of ESD protection diode 625. In one embodiment, watch case back 620 is connected the cathode of ESD protection diode 615 and 625. The exposed metal portions of the watch 610 are connected to the anode of ESD protection diode 615.

Voltage discharge circuitry 650 is connected between the heart rate monitor circuit 655 Vcc input and positive terminal of battery 635 and may be comprised of any circuitry or component that provides a high impedance path to electro static charge and/or transient voltage, such as for example one or more resistors, diodes or some other component.

The block diagram of FIG. 6 is configured with a pull-down configured micro-controller integrated circuit and with a single switch push button switch 640 corresponding to a push button as an example only.

The operation of the circuit of FIG. 6 is as follows. When the push button switch 640 is open (not depressed), the pull-down input is at a voltage level associated with ground as no current is flowing through R2 645.

Under normal operating conditions, a closed circuit loop is formed between circuit ground or battery negative terminal, heart rate monitor circuit 655, R1 voltage discharge circuit 650, and the positive terminal of battery 635. Since battery positive terminal is connected to watch module clamp 630 when push button 640 is depressed, there is a voltage drop across R2 645 corresponding to the voltage of the battery. The voltage at the pull-down input of the heart rate monitor circuit 655 becomes the voltage at the positive terminal of battery 635. Therefore, engaging push button 640 controls the logic signal at the pull-down input of 655. This logic signal can be used to turn on or off different modes of heart rate monitor circuit 655, such as for example the heart rate operating mode.

In some embodiments, when a resistor R1 is used to implement voltage discharge circuitry 650, the circuit is designed such that the value of the R1 resistor and current passing through the resistor is small enough to avoid causing a substantial voltage drop between Vcc and watch module clamp 630. However, the value should be high enough so that it can effectively impedes electro static charge from entering and damaging heart rate monitor circuit 655. As discussed above, choosing the impedance value for voltage discharge circuitry can be chosen based on these as well as other factors, and is a matter of design choice.

When an electrostatic discharge or other transient voltage discharge occurs at watch module clamp 630, the resistor R1 between clamp 630 and circuit Vcc input dissipates unwanted electro-static discharge and transient voltage discharges to protect heart rate monitor circuit 655. Additionally, majority of the charge may travel through ESD protection diode 625 which provides a lower impedance path than voltage discharge circuitry 650 to watch case back 620 and thus protects heart rate monitor circuitry 655.

When an electro static discharge or other transient voltage discharge occurs from watch case back 620, the charge travels through ESD protection diode 615 to the exposed metal sensors, and therefore bypasses heart rate monitor circuit 655. The charge can then be neutralized or dissipated to a nearby metallic or conductive object in contact with the exposed metal sensors on the watch top. As a result, the heart rate monitor circuit 655 is protected from any damage caused by electro static discharge or transient voltage discharge.

Figure 7:
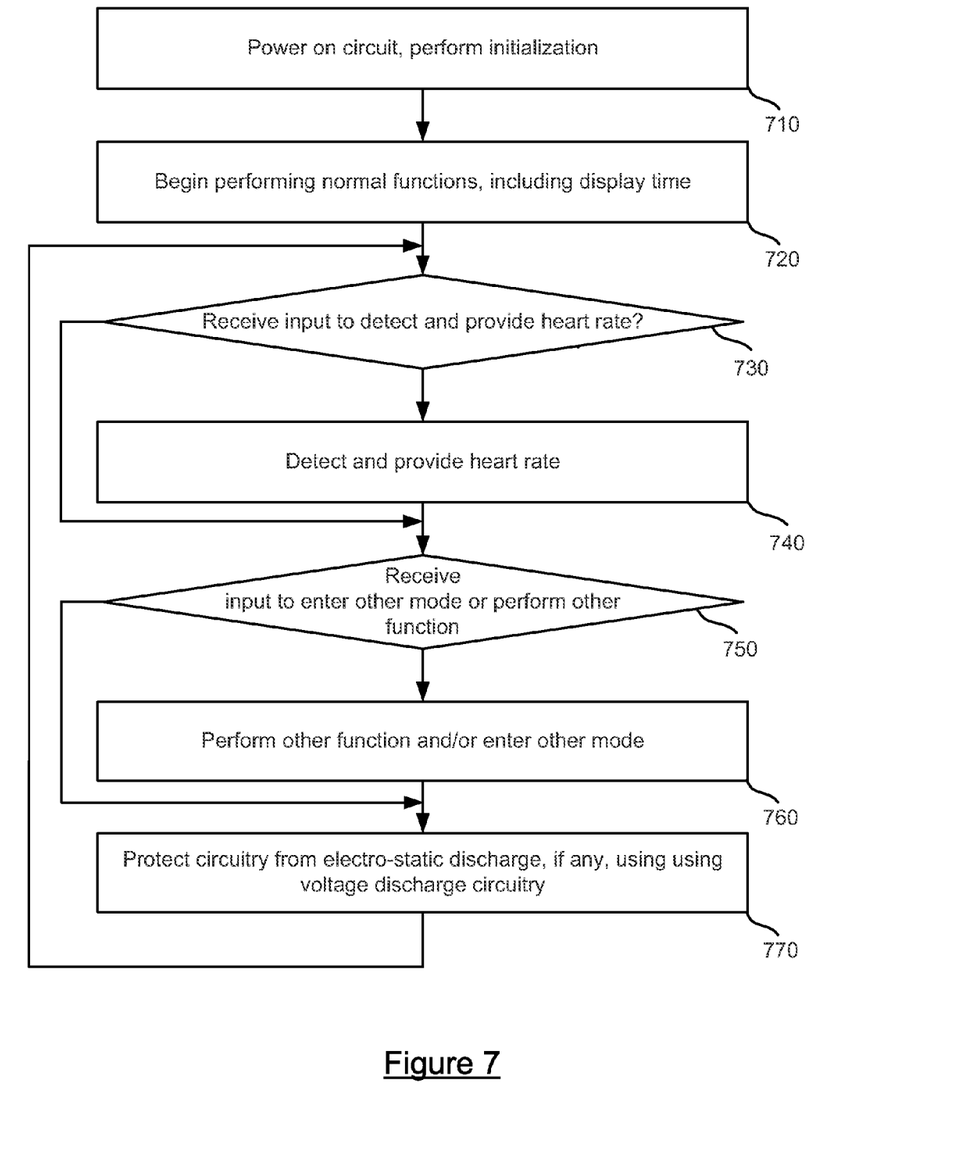
FIG. 7 is a flow chart of an embodiment of a method for protecting circuitry from electro static discharges.

FIG. 7 is a flow chart of an embodiment of a method for protecting circuitry from electro static discharge. First, the heart rate monitor circuit is powered on and an initialization is performed at step 710. For example, the circuit may be powered on by inserting a battery. An initialization may include determining that the battery has an appropriate level to operate the circuit and determine the current time. In some embodiments, power on and initialization may be performed from a sleep mode state.

The heart rate monitor then starts to perform normal functions including the display of time at step 720. The date may also be displayed as an initial function at step 720.

A determination is made as to whether input is received to detect and provide a heart rate for a user at step 730. The input may be a selection of one or more push-buttons 220 or some other mechanism on the watch. If input is received to detect and provide a heart rate, the heart rate is detected and provided at step 740. Detecting and providing a heart rate may require inquiring a pulse signal, determining the pulse component of the signal and determining the heart rate from the pulse component. Detecting and providing a heart rate is discussed in more detail in U.S. Pat. No. 5,876,350, filed on Nov. 7, 1996, having inventors Thomas Ying-Ching Lo and Yuh Show Tsai all of which are incorporated herein.

A determination is then made as to whether input is received to enter another mode or perform another function at step 750. The other mode or function input may be received as selection of a push-button 220 or some other input mechanism of the heart rate monitor. If input is not received at step 750, the method of FIG. 7 continues to step 770. If input is received, the other function and/or other mode is entered at step 760 in response to receiving the input.

At any time during the operation of the method of FIG. 7, circuitry within the heart rate monitor is protected from electro static discharge, transient voltage, or any other related voltage damage at step 770. The protection is implemented using voltage discharge circuitry components within the heart rate monitor. When an electro static voltage charge accumulates, the voltage may discharge through the voltage discharge circuitry (VDC). The VDC may be any circuitry that isolates the important watch circuitry to protect from the discharge and which also dissipates the electro static charge.

In some embodiments, the voltage discharge circuitry may be implemented as a resistor. Step 770 may be performed at any time during the operation of FIG. 7 including after power on, before power on or any other time.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

We claim:

1. A heart rate monitor, comprising:
   a monitor case;
   a case back configured to sense an electro-cardiogram signal and connected to the monitor case;
   a conducting clamp securing a battery, the battery having positive and negative terminals, the positive terminal connected to the conducting clamp;
   heart rate monitor circuitry for detecting a heart rate of a user, the heart rate monitor circuitry comprising a pull-down port, a voltage input and a ground terminal;
   a push button connected in a path between the pull-down port and the conducting clamp; and
   a first resistor connecting the voltage input of the heart rate monitor circuitry to the conducting clamp and to the positive terminal, the first resistor is configured to dissipate at least a portion of an electrostatic discharge from the conducting clamp, and the monitor case contains the heart rate monitor circuitry, conducting clamp and first resistor.

2. The heart rate monitor of claim 1, further comprising:
   an exposed sensor portion connected to the heart rate monitor circuitry; and
   an electrostatic discharge protection diode connecting the exposed sensor portion to the case back, the electrostatic discharge protection diode enabling electrostatic discharges to travel from the exposed sensor portion to the case back.

3. The heart rate monitor of claim 1, further comprising:
   an electrostatic discharge protection diode connecting the conducting clamp to the case back,
   the electrostatic discharge protection diode enabling electrostatic discharges to travel from the conducting clamp to the case back.

4. The heart rate monitor of claim 1, wherein the conducting clamp is a metal clamp.

5. The heart rate monitor of claim 1, further comprising:
   a second resistor between the push button and the pull-down port, connecting the path to ground.

6. The heart rate monitor of claim 3, wherein the electrostatic discharge protection diode is configured to pass accumulated charge from the conducting clamp to the case back.

7. The heart rate monitor of claim 1, wherein the push button extends outside the monitor case, and depression of the push button closes the path between the pull-down port and the conducting clamp, so that a voltage at the pull-down port becomes a voltage at the positive terminal, to change a state of the heart rate monitor circuitry.

8. The heart rate monitor of claim 5, wherein the push button extends outside the monitor case, and when the push button is not depressed, the path between the pull-down port and the conducting clamp is open, so that a voltage at the pull-down port is at ground.

9. The heart rate monitor of claim 1, wherein the heart rate monitor is a wrist worn device for detecting a pulse from a wrist of the user.

10. The heart rate monitor of claim 1, further comprising:
    a first electrostatic discharge protection diode connected between the conducting clamp and the case back; and
    a second electrostatic discharge protection diode connected between the heart rate monitor circuitry and the case back.

11. A heart rate monitor, comprising:
    a monitor case;
    a case back configured to sense an electro-cardiogram signal and attached to the monitor case;
    a conducting clamp securing a battery, the battery having positive and negative terminals, the negative terminal connected to the conducting clamp;
    heart rate monitor circuitry for detecting a heart rate of a user, the heart rate monitor circuitry comprising a pull-up port, a voltage input and a ground terminal, the voltage input is connected by a path to the positive terminal;
    a push button connected in a path between the pull-up port and the conducting clamp; and
    a first resistor connecting the ground terminal of the heart rate monitor circuitry to the conducting clamp, the first resistor is configured to dissipate electrostatic discharge charge from the conducting clamp and the monitor case contains the heart rate monitor circuitry, conducting clamp and first resistor.

12. The heart rate monitor of claim 11, further comprising:
    a first electrostatic discharge (ESD) protection diode connected between the conducting clamp and the case back, the first ESD protection diode configured to allow at least a portion of an electrostatic discharge to travel from the conducting clamp to the case back;
    an exposed sensor portion connected to the heart rate monitor circuitry; and
    a second ESD protection diode connecting the exposed sensor portion to the case back.

13. The heart rate monitor of claim 11, further comprising:
    a first electrostatic discharge (ESD) protection diode connected between the conducting clamp and the case back, the first ESD protection diode configured to allow at least a portion of an electrostatic discharge to travel from the conducting clamp to the case back;
    wherein the first resistor and the first ESD protection diode direct an electrostatic discharge occurring at the push button to the conducting clamp through an air gap between the push button and conducting clamp.

14. The heart rate monitor of claim 11, wherein the push button extends outside the monitor case, and when the push button is not depressed, the path between the pull-up port and the conducting clamp is open.

15. The heart rate monitor of claim 11, wherein the push button extends outside the monitor case, and depression of the push button closes the path between the pull-up port and the conducting clamp.

16. The heart rate monitor of claim 11, further comprising:
    a second resistor connecting the path to the pull-up port to the push button.

17. The heart rate monitor of claim 11, wherein heart rate monitor is a wrist worn device for detecting a pulse from a user's wrist.

18. A heart rate monitor, comprising:
- monitor circuitry for detecting a heart rate from a pulse signal;
- a clamp attached to a battery;
- a voltage discharge circuit connecting the clamp to the circuitry, the heart rate monitor configured to be worn on the wrist of a user; and
- an electro-static discharge protection diode connected between an external portion of the heart rate monitor and the clamp, the external portion of the monitor in contact with a user of the monitor.

19. The heart rate monitor of claim 18, wherein the voltage discharge circuit provides an electro-static discharge path away from the monitor circuitry.

20. The heart rate monitor of claim 18, wherein the voltage discharge circuit is a resistor.

* * * * *